United States Patent
Weeks, Jr. et al.

(10) Patent No.: US 11,333,339 B2
(45) Date of Patent: *May 17, 2022

(54) ANTIMICROBIAL LIGHT SOURCE ARRAY SYSTEM

(71) Applicant: Hubbell Lighting, Inc., Shelton, CT (US)

(72) Inventors: T. Warren Weeks, Jr., Simpsonville, SC (US); Avelino De Oliveira, Inman, SC (US)

(73) Assignee: Hubbell Lighting, Inc., Shelton, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/014,603

(22) Filed: Sep. 8, 2020

(65) Prior Publication Data
US 2020/0408394 A1 Dec. 31, 2020

Related U.S. Application Data

(63) Continuation of application No. 15/768,177, filed as application No. PCT/US2016/061234 on Nov. 10, 2016, now Pat. No. 10,767,843.
(Continued)

(51) Int. Cl.
*F21V 23/04* (2006.01)
*A61L 9/20* (2006.01)
(Continued)

(52) U.S. Cl.
CPC .......... *F21V 23/0471* (2013.01); *A61L 2/084* (2013.01); *A61L 2/10* (2013.01);
(Continued)

(58) Field of Classification Search
CPC ........ F21V 23/0471; A61L 2/084; A61L 2/10; A61L 9/20; A61L 2209/111; F21Y 2113/00
See application file for complete search history.

(56) References Cited

U.S. PATENT DOCUMENTS

| 8,398,264 B2 | 3/2013 | Anderson et al. |
| 9,039,966 B2 | 5/2015 | Anderson et al. |

(Continued)

FOREIGN PATENT DOCUMENTS

| JP | 2004301387 | 10/2004 |
| JP | 2007232323 | 9/2007 |
| WO | 2009056838 | 5/2009 |

OTHER PUBLICATIONS

MacLean et al., "405 nm light technology for the inactivation of pathogens and its potential role for environmental disinfection and infection control," The Journal of Hospital Infection, Sep. 2014, vol. 88, Issue 1—27 pages.
(Continued)

*Primary Examiner* — Karabi Guharay
(74) *Attorney, Agent, or Firm* — Michael Best & Friedrich LLP

(57) ABSTRACT

Systems and methods for controlling a light emitting diode (LED) system associated with an area and having a plurality of LED arrays are provided. In some implementations, the lighting system can include a first LED array associated with visible light and a second LED array associated with UV light. The lighting system can include one or more first sensors configured to detect occupancy within the area and send signals indicating whether the area is occupied. The lighting system can include one or more second sensors configured to detect microbes within an area and send signals indicating whether microbes are present in the area. The lighting system can include a control circuit configured to receive the signals sent by the one or more first and second sensors and to control the first LED array and the second LED array based on the signals.

19 Claims, 6 Drawing Sheets

Related U.S. Application Data

(60) Provisional application No. 62/253,208, filed on Nov. 10, 2015.

(51) Int. Cl.

| | |
|---|---|
| *F21S 8/00* | (2006.01) |
| *F21V 33/00* | (2006.01) |
| *A61L 2/08* | (2006.01) |
| *A61L 2/10* | (2006.01) |
| *F21Y 115/10* | (2016.01) |
| *F21W 131/205* | (2006.01) |
| *F21W 131/208* | (2006.01) |
| *F21Y 113/00* | (2016.01) |

(52) U.S. Cl.
CPC . *A61L 9/20* (2013.01); *F21S 8/03* (2013.01); *F21V 33/0068* (2013.01); *A61L 2202/14* (2013.01); *A61L 2202/25* (2013.01); *A61L 2209/111* (2013.01); *A61L 2209/12* (2013.01); *F21W 2131/205* (2013.01); *F21W 2131/208* (2013.01); *F21Y 2113/00* (2013.01); *F21Y 2115/10* (2016.08)

(56) References Cited

U.S. PATENT DOCUMENTS

| | | | |
|---|---|---|---|
| 9,333,274 B2 | 5/2016 | Peterson et al. | |
| 9,439,989 B2 | 9/2016 | Lalicki | |
| 9,700,641 B2 | 7/2017 | Hawkins et al. | |
| 9,927,097 B2 | 3/2018 | Lalicki et al. | |
| 10,767,843 B2 * | 9/2020 | Weeks, Jr. | F21V 23/0471 |
| 2002/0074559 A1 | 6/2002 | Dowling et al. | |
| 2003/0137258 A1 | 7/2003 | Piepgras et al. | |
| 2004/0141321 A1 | 7/2004 | Dowling et al. | |
| 2006/0221606 A1 | 10/2006 | Dowling et al. | |
| 2008/0008620 A1 * | 1/2008 | Alexiadis | F21S 4/26 422/24 |
| 2008/0137066 A1 | 6/2008 | Weinstein | |
| 2009/0168396 A1 | 7/2009 | Moriyasu et al. | |
| 2010/0246169 A1 | 9/2010 | Anderson | |
| 2010/0259917 A1 | 10/2010 | Ramer et al. | |
| 2011/0180687 A1 | 7/2011 | Rains, Jr. et al. | |
| 2013/0291735 A1 * | 11/2013 | Livchak | F24F 1/01 96/224 |
| 2013/0293156 A1 | 11/2013 | Wells | |
| 2014/0060096 A1 | 3/2014 | Shur | |
| 2014/0278136 A1 | 9/2014 | Shamsheyeva et al. | |
| 2015/0002027 A1 * | 1/2015 | Huang | H05B 47/105 315/153 |
| 2015/0273092 A1 | 10/2015 | Holub et al. | |
| 2016/0015840 A1 | 1/2016 | Gordon | |
| 2016/0030609 A1 | 2/2016 | Peterson et al. | |
| 2016/0030610 A1 | 2/2016 | Peterson et al. | |
| 2016/0361229 A1 | 12/2016 | Na | |
| 2016/0375161 A1 | 12/2016 | Hawkins | |
| 2016/0375162 A1 | 12/2016 | Marry | |
| 2016/0375163 A1 | 12/2016 | Hawkins et al. | |
| 2017/0006685 A1 | 1/2017 | Barron et al. | |
| 2017/0034889 A1 | 2/2017 | Primous et al. | |
| 2017/0080117 A1 | 3/2017 | Gordon | |
| 2018/0117193 A1 * | 5/2018 | Yadav | F21V 23/02 |

OTHER PUBLICATIONS

MacLean et al., "An Innovation: Decontamination by Light-HINS-light Environmental Decontamination System, A new method for pathogen control in the clinical environment," Microsoft Power Point, HINS-light EDS Presentation for Infection Prevention Scotland, The Robertson Trust Laboratory for Electronic Sterilisation Technologies (ROLEST), Oct. 27, 2010—20 pages.

Noimark et al., "Light-activated antimicrobial surfaces with enhanced efficacy induced by a dark-activated mechanism," Chemical Science, Issue 6, Jun. 1, 2014—1 page.

Wallace, John "HINS light kills surface bacteria in hospitals," Laser Focus World, http://www.laserfocusworld.com/articles/2010/11/hins-light-kills-surface.html, accessed on Oct. 30, 2017, PennWell Corporation, Tulsa, OK, Nov. 15, 2010—2 pages.

MacLean et al., "Environmental decontamination of a hospital isolation room using high-intensity narrow-spectrum light," The Hospital Infection Society, Elsevier Ltd., Nov. 2010;76(3)—1 page.

Kenall Mfg. Launches New Bacteria-killing LED Light for Hospitals, LEDinside, a Business Division of TrendForce Corp., Jun. 29, 2015, accessed on Oct. 30, 2017, http://www.ledinside.com/products/2015/6/kenall_manufacturing_launches_new_uv_led_light_for_hospitals—3 pages.

PCT International Search Report and Written Opinion for corresponding PCT Application No. PCT/US2016/061234, dated Jan. 13, 2017—12 pages.

Extended European Search Report for corresponding EP Application No. 16864964.8, dated Jul. 11, 2018—9 pages.

PCT International Preliminary Reporton Patentability for corresponding PCT Application No. PCT/US2016/061234, dated May 15, 2018—11 pages.

* cited by examiner

ANTIMICROBIAL LIGHT SOURCE ARRAY SYSTEM

PRIORITY CLAIM

The present application is a continuation of U.S. application Ser. No. 15/768,177, filed on Apr. 13, 2018, which is a U.S. 371 of PCT/US2016/061234, filed Nov. 10, 2016, which claims the benefit of priority of U.S. Provisional Application Ser. No. 62/253,208, filed on Nov. 10, 2015, which are all incorporated herein by reference.

FIELD

The present disclosure relates generally to lighting systems, and more particularly to lighting systems that can provide antimicrobial functions.

BACKGROUND

Microbes often exist in environments intended to be clean and free from microorganisms. Ultraviolet (UV) light illumination has been shown to exhibit antimicrobial functions because it can eliminate microbes as well as prohibit germ and mold growth.

LED lighting systems can include one or more LED devices that become illuminated as a result of the movement of electrons through a semiconductor material. LED devices are becoming increasingly used in many lighting applications and have been integrated into a variety of products, such as light fixtures, indicator lights, flashlights, and other products. LED lighting systems can provide increased life and durability, can produce less heat, and can provide other advantages relative to traditional incandescent and fluorescent lighting systems. Moreover, the efficiency of LED lighting systems has increased such that higher power can be provided at lower cost to the consumer.

LED lighting systems can include LED devices that can emit UV light. LED lighting systems with UV LED devices can be installed in areas to help reduce and prevent the presence of microbes. However, exposure to UV light wavelengths can, in some cases, be detrimental to humans, degrade plastic components and finishes, as well as diminish furnishings. Moreover, full time UV light illumination can impact the color temperature of the light source and make it more difficult to get a desired color temperature from the given LED device.

SUMMARY

Aspects and advantages of embodiments of the present disclosure will be set forth in part in the following description, or can be learned from the description, or can be learned through practice of the embodiments.

One example aspect of the present disclosure is directed to a lighting system. The lighting system includes a first light source configured to emit visible light and a second light source configured to emit UV light. The system can include one or more first sensors configured to detect occupancy within an area. The system can include one or more second sensors configured to detect microbe presence within the area. The system can include a control circuit configured to control the first light source and the second light source based at least in part on a first signal received from the one or more first sensors and a second signal received from the one or more second sensors.

Other example aspects of the present disclosure are directed to systems, methods, apparatus, circuits, and electronic devices for controlling a lighting system which can provide UV light for antimicrobial functions.

These and other features, aspects and advantages of various embodiments will become better understood with reference to the following description. The accompanying drawings, which are incorporated in and constitute a part of this specification, illustrate embodiments of the present disclosure and, together with the description, serve to explain the related principles.

BRIEF DESCRIPTION OF THE DRAWINGS

Detailed discussion of embodiments directed to one of ordinary skill in the art are set forth in the specification, which makes reference to the appended figures, in which.

DETAILED DESCRIPTION

Figure 1:
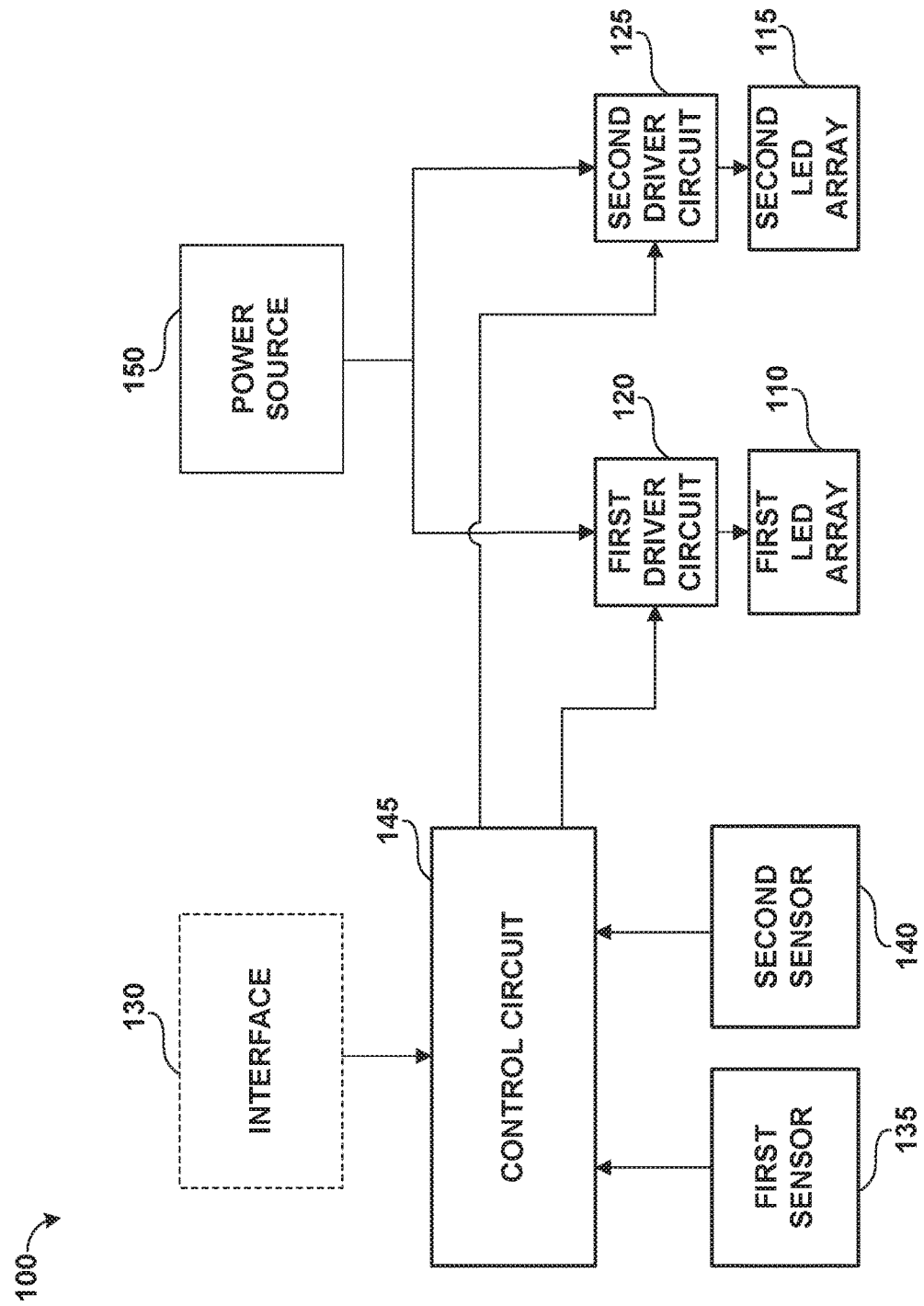
FIG. 1 depicts an example LED lighting system according to example embodiments of the present disclosure.

Reference now will be made in detail to embodiments, one or more examples of which are illustrated in the drawings. Each example is provided by way of explanation of the embodiments, not limitation of the present disclosure. In fact, it will be apparent to those skilled in the art that various modifications and variations can be made to the embodiments without departing from the scope or spirit of the present disclosure. For instance, features illustrated or described as part of one embodiment can be used with another embodiment to yield a still further embodiment. Thus, it is intended that aspects of the present disclosure cover such modifications and variations.

Example aspects of the present disclosure are directed to controlling a plurality of light sources in a lighting system to provide antimicrobial functions by, for instance, controlling the timing at which UV light and/or visible light are emitted from the lighting system. The lighting system can be associated with an area intended to be free from microbes, such as a hospital room, recovery room, clean room, laboratory, home, etc. The lighting system can limit the emission of UV light to a time period when microbes are present within the area and the area is unoccupied, thereby avoiding human exposure and unnecessary UV light source activation. The lighting system can further limit the emission of visible light to when the area is occupied or when visible light is otherwise desirable (e.g., for external observation of the area). As used herein, a lighting system can include, but is not limited to, one or more of a lighting circuit, light engine, one or more luminaires, one or more light fixtures, a plurality of lighting devices arranged in an environment, a combination of any of the foregoing, or other system use to provide illumination. The use of the term "about" in conjunction with a numerical value refers to within 5% of the stated numerical value.

Figure 3:
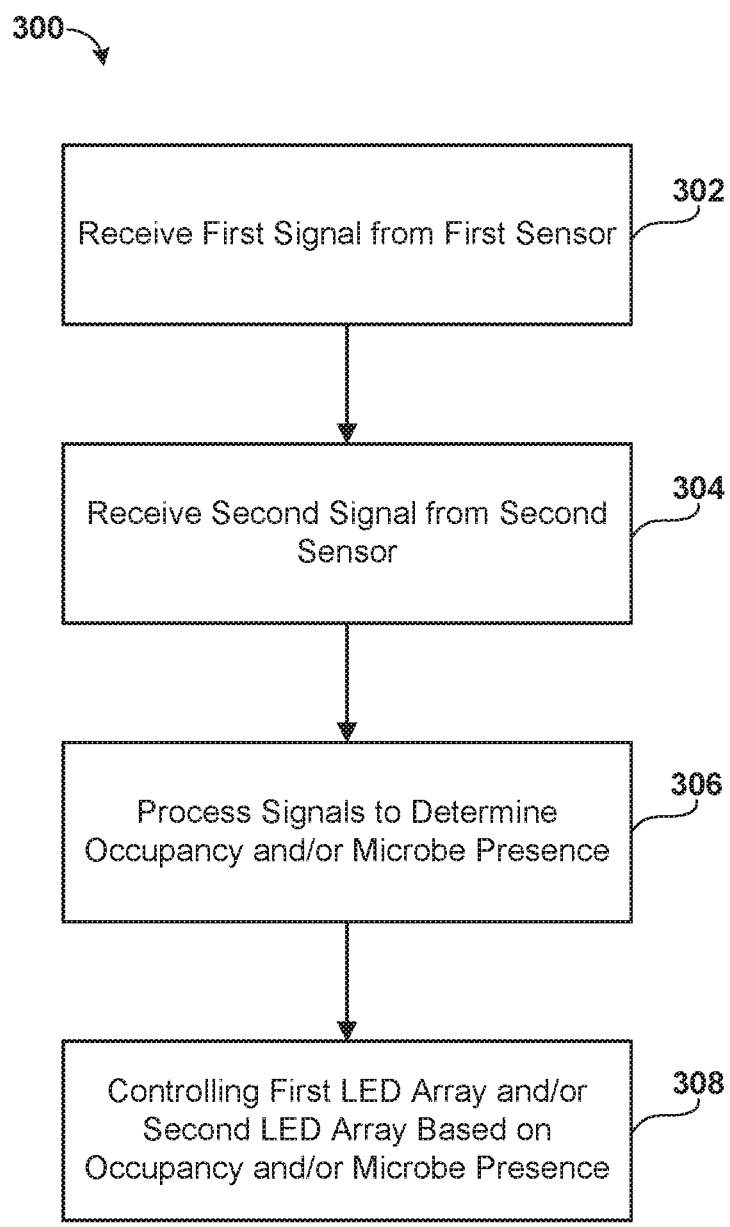
FIG. 3 depicts a flow diagram of an example method according to example embodiments of the present disclosure.
Figure 4:
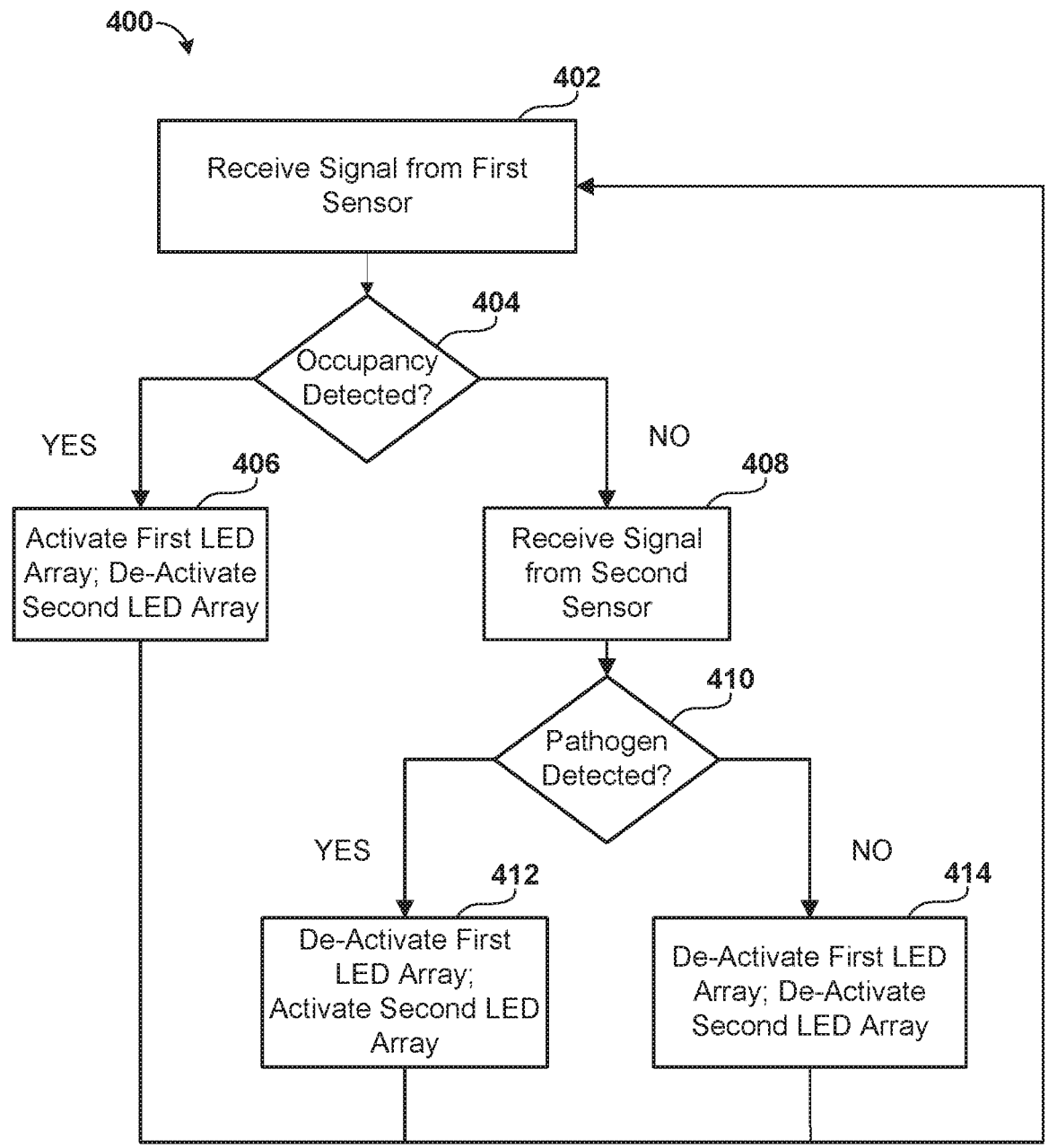
FIG. 4 depicts a flow diagram of an example method according to example embodiments of the present disclosure.

A light emitting diode (LED) lighting system can include a first LED array associated with and configured to emit visible light and a second LED array associated with and configured to emit UV light. As used herein, UV light can include ultraviolet light (e.g., wavelength from about 100 nm to about 400 nm) and near ultraviolet light (e.g., associated with wavelength from about 400 nm to about 415 nm, such as about 405 nm). Visible light can include light having a wavelength ranging from about 400 nm to about 700 nm, such as light having a wavelength ranging from about 420 nm to about 700 nm. The LED lighting system can include means for controlling the first LED array (e.g., associated with visible light) and/or the second LED array (e.g., associated with UV light) based on occupancy and/or microbe presence to control the emission of UV light. For example, the LED lighting system can include a control circuit configured to activate or de-activate the first LED array (e.g., associated with visible light) and/or the second LED array (e.g., associated with UV light) based on occupancy and/or microbe presence to control the emission of UV light. Example means for controlling the first LED array and second LED array based on occupancy and/or microbe presence are discussed in FIGS. 1 and 2. Example control methods associated with the means for controlling the first LED array and the second LED array are illustrated in FIGS. 3 and 4.

Example aspects of the present disclosure are discussed with reference to an LED lighting system for purposes of illustration and discussion. Those of ordinary skill in the art, using the disclosures provided herein, will understand that example aspects of the present disclosure can be used with lighting systems associated with a variety of different types of light sources (e.g., fluorescent light sources) without deviating from the scope of the present disclosure.

An LED lighting system according to example aspects of the present disclosure can include one or more first sensors configured to detect whether an area is occupied by a human or other animal. The one or more first sensors can include one or more motion sensors, position sensors, acoustic sensors, infrared sensors, temperature sensors, electric eye sensors, or any sensors that are suitable to detect whether an area is occupied by a human or other animal. The one or more first sensors can be configured to send a first signal to the control circuit indicating whether the area is occupied. The system can include one or more second sensors configured to detect microbes, pathogens, bacteria, viruses, parasites, and/or germs (hereinafter, generally referred to as "microbes") within an area. The one or more second sensors can be configured to send a second signal to the control circuit indicating whether a threshold amount of microbes are present in the area.

The control circuit can be configured to process the first signal and the second signal to determine a control scheme for operation of the first LED array and/or the second LED array. A control scheme can specify the operation of the first and/or second LED arrays based on the signals from the first and/or second sensors. As one example, if it is determined based on a signal from the first sensor that the area is occupied, the control circuit can control the first driver circuit to provide a driver output to the first LED array sufficient to activate the first LED array to emit visible light. In addition, if the second LED array is currently activated, the control circuit can send a signal to the second driver circuit to cease providing or to reduce current to the second LED array to de-activate the second LED array and prohibit or reduce the emission of UV light while the area is occupied.

As another example, if it is determined that the area is unoccupied and that the number of microbes present in the area exceed a threshold, the control circuit can control the second driver circuit to provide a driver output to the second LED array sufficient to activate the second LED array to emit UV light (e.g., causing antimicrobial effects on the detected microbes). If desired, the control circuit can send a signal to the first driver circuit to cease providing or to reduce current to the first LED array sufficient to de-activate the first LED array and prohibit the emission of visible light to reduce unnecessary use of the first LED array. If it is determined that microbes are not present in the area and the area is unoccupied, the control circuit can control the first driver circuit and the second driver circuit to cease providing or to reduce current to the first LED array and the second LED array to de-activate both the first LED array and the second LED array.

Controlling the emission of UV light from a UV LED array according to example aspects of the present disclosure can assist with reduction of microbes within an area and can reduce the need for antimicrobial coatings. In addition, the need for moisture for the purpose of antimicrobial effects can be reduced, which can increase the ability to kill both gram-negative and gram-positive microbes. De-activating a UV LED array when an area is occupied can help avoid human UV light exposure. Moreover, limiting activation of the UV LED array based on the amount and presence of microbes in the area can extend the life and color of the LED array by reducing unnecessary illumination.

With reference now to the FIGS., example embodiments of the present disclosure will be discussed in detail. FIG. 1 depicts an example LED lighting system 100 according to example embodiments of the present disclosure. The LED lighting system 100 can include a first LED array 110, a second LED array 115, a first driver circuit 120, a second driver circuit 125, an interface 130, one or more first sensors 135, one or more second sensors 140, and a control circuit 145. A power source 150 can supply AC or DC power to the LED lighting system 100. The control circuit 145 can be in communication with the first driver circuit 120, the second driver circuit 125, the interface 130, the one or more first sensors 135, and the one or more second sensors 140. Two LED arrays are illustrated in FIG. 1 for purposes of illustration and discussion. Those of ordinary skill in the art, using the disclosures provided herein, will understand that any number of LED arrays can be used in the LED lighting system 100 without deviating from the scope of the present disclosure.

Each of the first LED array 110 and the second LED array 115 can include one or more LED devices. The LED devices can emit light as a result of electrons moving through a semiconductor material. The first LED array 110 can be associated with visible light and can include one or more LED devices configured to emit visible light (or other light or electromagnetic radiation not within the UV spectrum). The second LED array 115 can be associated with UV light and can include one or more LED devices configured to emit UV light (e.g., electromagnetic radiation within the UV spectrum).

The first driver circuit 120 can be associated with the first LED array and the second driver circuit 125 can be associated with the second LED array 115. Each of the first driver circuit 120 and the second driver circuit 125 can be configured to receive an input power, such as an input AC power or an input DC power, and can convert the input power to a suitable driver output for powering the first LED array 110 and the second LED array 115, respectively. Each of the first driver circuit 120 and the second driver circuit 125 can include any suitable LED driver circuit and can include various components, such as switching elements (e.g., transistors) that are controlled to provide a suitable driver output. For instance, in one embodiment, the first and/or second driver circuits 120, 125 can include one or more transistors. Gate timing commands can be provided to the one or more transistors to convert the input power to a suitable driver output using pulse width modulation techniques. As discussed in detail below, each of the first driver circuit 120 and the second driver circuit 125 can be configured to adjust the driver output based at least in part on a signal received from control circuit 145. Other suitable driver circuits can be used without deviating from the scope of the present disclosure.

The interface 130 can be provided to control the first LED array and/or the second LED array. The interface 130 can include one or more components for communicating a lighting control signal to the control circuit 145. In example embodiments, the interface 130 can be configured to allow a user to manually control aspects (e.g., dim) the first LED array 110 and/or the second LED 115 array based on a lighting control signal. Additionally, and/or in the alternative, the interface 130 can be configured to allow a user to manually activate and/or de-activate the first LED array 110 and/or the second LED array 115, as desired. The interface 130 can be associated with a light control panel, manual dimmer, or other suitable control system. The lighting control signal can be a 0V to 10V lighting control signal, DALI control signal, DMX control signal or other suitable control signal.

The one or more first sensors 135 can be configured to detect occupancy (e.g., human or other animal occupancy) within an area. The one or more first sensors 135 can include one or more motion sensors, position sensors, acoustic sensors, infrared sensors, temperature sensors, electric eye sensors, or any other sensors that are suitable to detect whether an area is occupied by a human or other animal. The one or more first sensors 135 can be configured to send a signal to the control circuit 145. For instance, the one or more first sensors 135 can send a signal to the control circuit 145 indicating whether the area is occupied (e.g., when movement, sound, heat, other condition change indicative of human and/or animal presence has been detected within the area).

The one or more second sensors 140 can be configured to detect microbes within an area. The one or more second sensors 140 can be configured to send a signal to the control circuit 145. For instance, the one or more second sensors 140 can send a signal to the control circuit 145 indicating whether a threshold amount of microbes (e.g., the number of microbes is sufficient to be detected by the sensor) have been detected in the area.

In example embodiments, the one or more second sensors 140 can include one or more microbe concentrating devices and one or more biosensors. The one or more microbe concentrating devices can, for instance, include RNA strand samples of specific microbes for detection on the one or more biosensors. In particular example implementations, the one or more biosensors can include a multiplexing DNA electrochemical biosensor that can generate electrical signals in proportion to the concentration of individual target microbes. For instance, the RNA strands can be delivered to DNA probes that are attached to individual electrodes of a biosensor. Each electrode can be pre-fabricated with DNA probes from a specific microbe. A biosensor can detect a particular microbe when RNA from the sample hybridizes with complementary DNA probes. Voltammetry scans can be applied on each electrode. The electrodes where hybridization takes place can cause chemicals (e.g., guanine) to oxidize and subsequently generate electrical current. The peak of the current can be measured against background noise to determine if the electrode's specified microbe is present, and against currents from known samples to determine the concentration of the specified microbe. This can be done simultaneously, for each electrode, to measure the presence and concentration of multiple microbes in the area. Those of ordinary skill in the art, using the disclosure provided herein, will understand that other types of microbe sensors can be used without deviating from the scope of the present disclosure.

In some embodiments, the one or more second sensors 140 can include one or more indicators for indicating the presence of microbes. The one or more indicators can be, for instance, visual or audio indicators. For instance, in some embodiments, the one or more indicators can provide a visual indication (e.g., a change of colors) based on detected microbe presence. In some embodiments, an LED signal can be triggered, such as a visual LED signal or infrared LED signal. In some embodiments, the indicator can be communicated as electronic data over, for instance, suitable communication means or media.

The control circuit 145 can include one or more control devices, such as one or more microcontrol circuits, microprocessors, logic devices, integrated circuits, or other control devices. The one or more control devices can include one or more memory devices. In another embodiment, an application specific integrated circuit (ASIC) is contemplated. The control circuit 145 can be configured to send, receive, and/or process signals to and/or from the one or more first sensors 135, the one or more second sensors 140, the first driver circuit 120, the second driver circuit 125, and the interface 130.

The signals from the one or more first sensors 135 and/or the one or more second sensors 140 can be communicated to the control circuit 145 or other aspects of the system using any suitable communication means or media, such as wired and/or wireless communication means. For instance, in some embodiments, signals can be communicated from the one or more second sensors 140 wirelessly, through light communication, or other non-wired or wired means.

The control circuit 145 can be configured to control the first and second driver circuits 120, 125 in communication with the first and second LED arrays 110, 115 to control the driver output (e.g., driver current) supplied to the first and second LED arrays 110, 115. For instance, the control circuit 145 can receive a first signal from the one or more first sensors 135 indicating that the area is occupied (e.g., when movement, sound, heat, other condition change has been detected within the area). Additionally, or alternatively, the control circuit 145 can receive a second signal from the one or more second sensors 140 indicating that microbes have been detected within the area. The control circuit 145 can process the first and second signals and, based on the processed signals, determine a control scheme for controlling the first and second LED arrays 110, 115.

For instance, in one embodiment, if the control circuit 145 determines (e.g., based on the first signal) that the area is occupied, the control circuit 145 can send a signal to the first driver circuit 120 to control the first driver circuit 120 to provide a driver output to the first LED array 110 sufficient to activate the first LED array 110 to emit visible light. In addition, and/or in the alternative, the control circuit 145 can send a signal to the second driver circuit 125 to control the second driver circuit 125 to provide a driver output to the second LED array 115 that de-activates the second LED array 115 and ceases and/or prohibits the emission of UV light.

In one embodiment, if the control circuit 145 determines (e.g., based on the first and second signals) that the area is not occupied and that microbes are present in the area, the control circuit 145 can send a signal to the first driver circuit 120 to control the first driver circuit 120 to provide a driver output to the first LED array 110 that de-activates the first LED array 110 and ceases and/or prohibits the emission of visible light. The control circuit 145 can further send a signal to the second driver circuit 125 to control the second driver circuit 125 to provide a driver output to the second LED array 115 sufficient to activate the second LED array 115 to emit UV light for antimicrobial effects. If visible light is desired, the control circuit 145 can send a signal to the first driver circuit 120 to provide a driver output to the first LED array 110 sufficient to activate the first LED array 110 to emit visible light. Other suitable control schemes are contemplated by the present disclosure.

Figure 2:
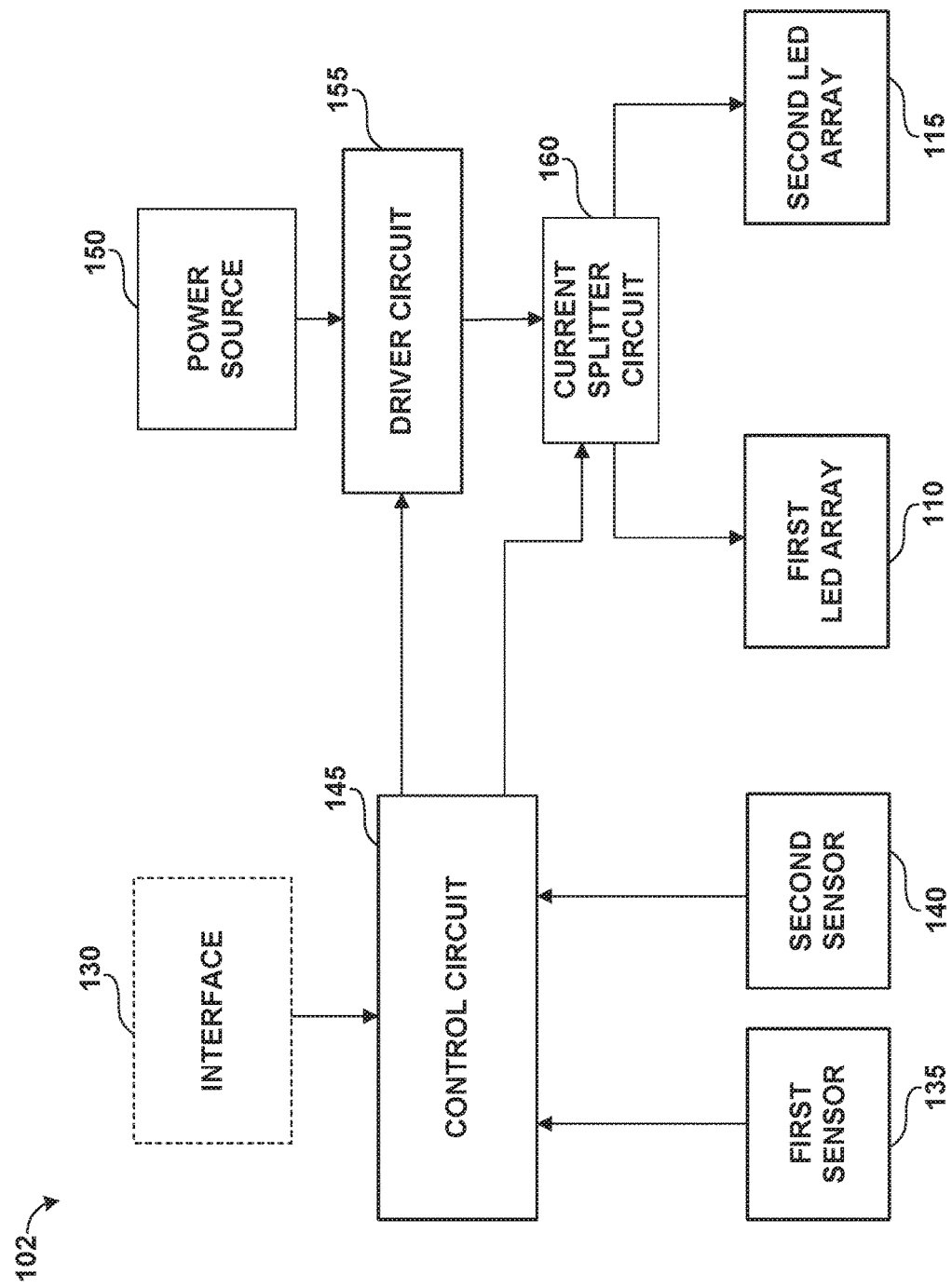
FIG. 2 depicts an example LED lighting system according to example embodiments of the present disclosure.

FIG. 2 depicts an example embodiment of a lighting system according to example embodiments of the present disclosure. FIG. 2 depicts an example LED lighting system 102 that includes many similar elements to the LED lighting system 100 of FIG. 1. For instance, the lighting system 102 includes a first LED array 110, a second LED array 115, an interface 130, one or more first sensors 135, one or more second sensors 140, and a control circuit 145. A power source 150 can supply AC or DC power to the LED lighting system 102. Additionally, and/or alternatively, the LED lighting system 102 can include a driver circuit 155 and a current splitter circuit 160.

As illustrated in FIG. 2, a driver output from the driver circuit 155 can be provided to a current splitter circuit 160. The current splitter circuit 160 can be configured to split the driver output into a first current for powering the first LED array 110 and a second current for powering the second LED array 115. In this way, the current splitter circuit 160 can be used to adjust the lumen output of the first LED array 110 relative to the lumen output of the second LED array 115.

The current splitter circuit 160 can be configured to control the current ratio of the first current provided to the first LED array 110 to the second current provided to the second LED array 115 based on a control signal that can be provided by the control circuit 145. For instance, according to example embodiments of the present disclosure, the control circuit 145 can provide one or more control signals to the current splitter circuit 160 to control the ratio of the first current provided to the first LED array 110 and the second current provided to the second LED array 120 based on signals from the one or more first sensors 135 and the one or more second sensors 140.

For instance, in one embodiment, if the control circuit 145 determines (e.g., based on the first signal) that the area is occupied, the control circuit 145 can send a signal to the current splitter 160 to control the current splitter 160 such that a majority of the light emitted from the LED lighting system 102 is emitted from the first LED array 110 (e.g., visible light) and a reduced amount (e.g., zero light emission, de minimis, minority, etc.) of UV light is emitted from the second LED array 115.

In one embodiment, if the control circuit 145 determines (e.g., based on the first and second signals) that the area is not occupied and that a threshold amount of microbes are present in the area, the control circuit 145 can send a signal to the current splitter 160 to control the current splitter 160 such that a reduced amount (e.g., zero light emission, de minimis, minority, etc.) of visible light is emitted from the first LED array 110 and such that a majority of the light emitted from the LED lighting system 102 is emitted from the second LED array 115 (e.g., UV light). Other suitable control schemes can be used based on the signals from the one or more first sensors and the one or more second sensors according to example embodiments of the present disclosure.

FIG. 3 depicts a flow diagram of an example method 300 for controlling an LED lighting system according to example embodiments of the present disclosure. The method 300 will be discussed with reference to the LED lighting system 100 of FIG. 1 but can be implemented with other suitable lighting systems. In addition, FIG. 3 depicts steps performed in a particular order for purposes of illustration and discussion. Those of ordinary skill in the art, using the disclosures provided herein, will understand that the steps of any of the methods disclosed herein can be modified, adapted, expanded, omitted, and/or rearranged in various ways without deviating from the scope of the present disclosure.

At (302), the method includes receiving a first signal from the one or more first sensors 135. For instance, the control circuit 145 can receive a signal from the one or more first sensors 135 indicating whether the area is occupied (e.g., when movement, sound, heat, other condition change has been detected within the area). At (304), the method includes receiving a second signal from the one or more second sensors 140. For instance, the control circuit 145 can receive a second signal from the one or more second sensors 140 indicating that microbes have been detected in the area.

At (306), the method includes processing, by the control circuit 145, the first and second signals to determine whether the area is occupied and/or whether microbes are present in the area. For instance, the control circuit 145 can process the first signal to determine whether the room is occupied. The control circuit 145 can process the second signal to determine whether a threshold amount of microbes are present in the area. Based on the processed signals, the control circuit 145 can determine a control scheme for the first LED array 110 (configured to emit visible light) and/or the second LED array 115 (configured to emit UV light). The control scheme can specify activation and deactivation for the first LED array 110 and the second LED array 115. An example control scheme will be discussed with reference to FIG. 4.

At (308) of FIG. 3, the method includes controlling the first LED array 110 and/or the second LED array 115 based on whether the area is occupied and/or microbes are present. For instance, the control circuit 145 can provide control signals to one or more driver circuits, current splitter circuits, etc. to control the light emitted by the first LED array 110 and/or the second LED array 115 in accordance with the control scheme.

FIG. 4 depicts a flow diagram of an example method 400 for controlling a first LED array and a second LED array based on occupancy and microbe presence according to example embodiments of the present disclosure. The method 400 will be discussed with reference to the LED lighting system 100 of FIG. 1 but can be implemented with other suitable lighting systems. In addition, FIG. 4 depicts steps performed in a particular order for purposes of illustration and discussion. Those of ordinary skill in the art, using the disclosures provided herein, will understand that the steps of any of the methods disclosed herein can be modified, adapted, expanded, omitted, and/or rearranged in various ways without deviating from the scope of the present disclosure.

At (402), the method 400 includes receiving a first signal from the one or more first sensors 135. For instance, the control circuit 145 can receive a signal from the one or more first sensors 135 indicating whether the area is occupied (e.g., when movement, sound, heat, other condition change has been detected within the area). At (404), the method 400 includes processing, by the control circuit 145, the first signal to determine if the area is occupied. If it is determined that the area is occupied, at (406), the method 400 includes activating the first LED array 110 (configured to emit visible light) and, if necessary, de-activating the second LED array 115 (configured to emit UV light). For instance, the control circuit 145 can send a signal to the first driver circuit 120 to control the first driver circuit 120 to provide a driver output to the first LED array 110 sufficient to activate the first LED array 110 to emit visible light. If the second LED array 115 is currently activated, the control circuit 145 can send a signal to the second driver circuit 125 to control the second driver circuit 125 to provide a driver output to the second LED array 115 that de-activates the second LED array 115 and prohibits or reduces the emission of UV light.

At (408), if it is determined that the area is unoccupied, the method 400 includes receiving a second signal from the one or more second sensors 140. For instance, the control circuit 145 can receive a signal from the one or more second sensors 140 indicating whether microbes have been detected in the area. At (410), the method 400 includes processing, by the control circuit 145, the second signal to determine if microbes are present in the area. If it is determined that the microbes are present in the area, at (412), the method 400 includes de-activating the first LED array 110 (configured to emit visible light), if necessary, and activating the second LED array 115 (configured to emit UV light). For instance, if the first LED array 110 is currently activated, the control circuit 145 can send a signal to the first driver circuit 120 to control the first driver circuit 120 to provide a driver output to the first LED array 110 that de-activates the first LED array 110 and prohibits the emission of visible light. The control circuit 145 can send a signal to the second driver circuit 125 to control the second driver circuit 125 to provide a driver output to the second LED array 115 sufficient to activate the second LED array 115 to emit UV light (e.g., for antimicrobial effects). Alternatively, if visible light is desired and the first LED array 110 is currently de-activated, the control circuit 145 can send a signal to the first driver circuit 120 to control the first driver circuit 120 to provide a driver output to the first LED array 110 sufficient to activate the first LED array 110 to emit visible light.

If it is determined that microbes are not present in the area, at (414), the method 400 includes de-activating the first LED array 110 and de-activating the second LED array 115. For instance, the control circuit 145 can send a signal to the first driver circuit 120 and a signal to the second driver circuit 125 to control the first and second driver circuits 120, 125 to provide driver outputs to the first LED array 110 and the second LED array 115 that de-activate the first LED array 110 and the second LED array 115. Alternatively, if visible light is desired, the control circuit 145 can send a signal to the first driver circuit 120 to control the driver circuit 120 to provide a driver output to the first LED array 110 sufficient to activate the first LED array 110 to emit visible light.

Figure 5:
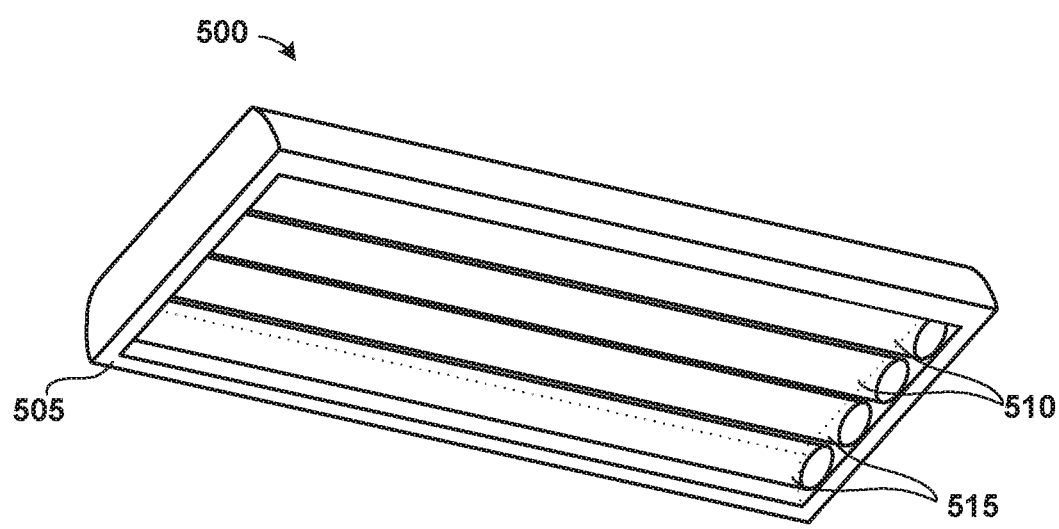
FIG. 5 depicts an example LED lighting unit according to example embodiments of the present disclosure.

FIG. 5 depicts an example lighting unit 500 that can include an LED circuit according to example embodiments of the present disclosure. The lighting unit 500 can include a housing 505 used to house and protect various components of the lighting unit. The housing 505 can be constructed of any suitable material, such as anodized aluminum, steel, or plastic.

The lighting unit 500 can include one or more first light sources 510. The one or more first light sources 510 can include LED devices that are configured to emit light as a result of electrons moving through a semiconductor material. In particular implementations, the one or more first light sources 510 can include an LED array (e.g., similar to the first LED array 110) associated with and configured to emit visible light. While the present subject matter is discussed with reference to the first light source(s) 510 including one or more LED devices, those of ordinary skill in the art, using the disclosures provided herein, will understand that the first light source(s) 510 can be other types of light sources, such as fluorescent light sources or incandescent light sources, without deviating from the scope of the present disclosure, with each combination providing its own benefits.

The lighting unit 500 can further include one or more second light sources 515. The one or more second light sources 515 can include LED devices that are configured to emit light as a result of electrons moving through semiconductor material. In particular implementations, the one or more second light sources 515 can include an LED array (e.g., similar to the second LED array 115) associated with and configured to emit UV light. Additionally, and/or alternatively, the second lights source(s) 515 can include other types of light sources.

In some embodiments, the lighting unit 500 can include reflectors, lenses, and/or other optics (not shown) in conjunction with lighting unit 500 to provide a desired light distribution from the first light source(s) 510 and/or the second light source(s) 515. For example, the lighting unit 500 can include a lens disposed over an aperture, such as a glass, polycarbonate, acrylic, or silicone lens or other suitable lens.

Figure 6:
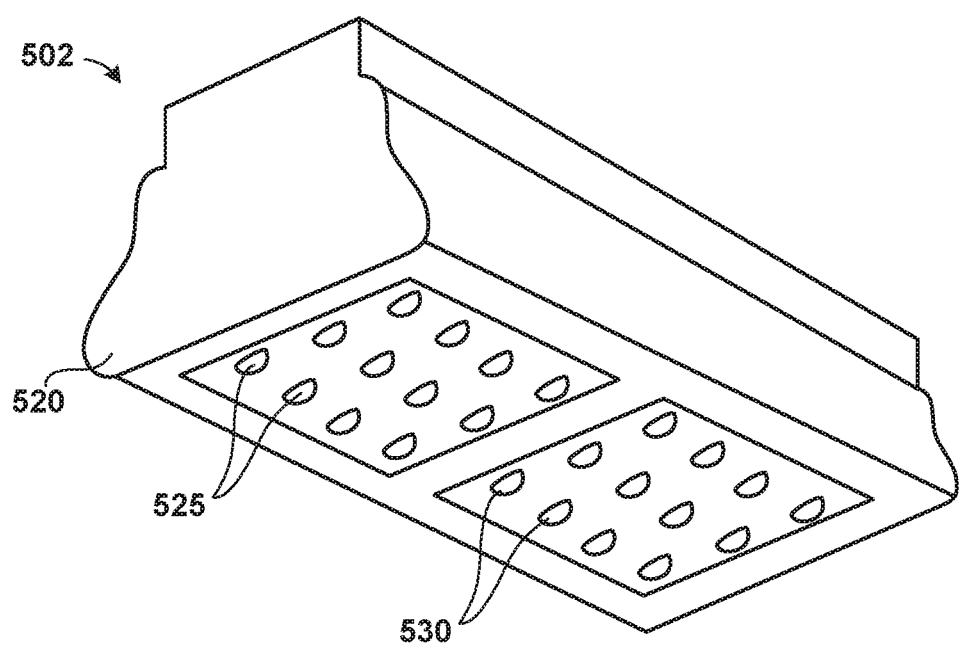
FIG. 6 depicts an example LED lighting unit according to example embodiments of the present disclosure.

FIG. 6 shows another example lighting unit 502 that can include an LED circuit according to example embodiments of the present disclosure. The lighting unit 502 can include a housing 520 used to house and protect various components of the lighting unit. The housing 520 can be constructed of any suitable material, such as anodized aluminum, steel, or plastic. The lighting unit 502 can receive one or more first light sources 525 and one or more second light sources 530, in a manner similar to lighting unit 500. The one or more first light sources 525 can include a first LED array (e.g., similar to the first LED array 110) associated with and configured to emit visible light. The one or more second light sources 530 can include a second LED array (e.g., similar to the second LED array 115) associated with and configured to emit UV light. In particular implementations, each of the one or more first light sources 525 and/or second light sources 530 can include an LED board having a plurality of LED devices. Additionally, and/or alternatively, the first lights source(s) 525 and/or the second light source(s) 530 can include other types of light sources.

While the present subject matter has been described in detail with respect to specific example embodiments thereof, it will be appreciated that those skilled in the art, upon attaining an understanding of the foregoing can readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art.

What is claimed is:

1. A lighting system, comprising:
   a first light source configured to emit visible light in an area;
   a second light source configured to emit UV light in the area;
   one or more sensors configured to detect a condition within the area;
   a control circuit configured to control the first light source and the second light source based at least partially on an output from said one or more sensors;
   a driver circuit configured to receive one or more control signals from said control circuit; and
   a current splitter circuit configured to control a ratio of a first current provided to the first light source relative to the second light source.

2. The lighting system of claim 1, wherein the UV light has a wavelength in the range of about 100 nm to about 400 nm.

3. The lighting system of claim 2, wherein the visible light has a wavelength above about 400 nm.

4. The lighting system of claim 2, wherein the UV light has a wavelength between about 200 nm and about 300 nm.

5. The lighting system of claim 4, wherein the UV light has a wavelength between about 220 nm and about 285 nm.

6. The lighting system of claim 1, wherein the one or more sensors include at least one first sensor that detects occupancy and at least one second sensor that detects a presence of microbes.

7. The lighting system of claim 6, wherein the at least one first sensor includes one or more motion sensors; position sensors, acoustic sensors, infrared sensors, temperature sensors, or electric eye sensors.

8. The lighting system of claim 6, wherein the at least one second sensor includes at least a microbe concentrating device and a biosensor.

9. The lighting system of claim 1, wherein said first light source includes one or more light emitting diodes (LED) and said second light source includes one or more light emitting diodes (LED).

10. The lighting system of claim 1, wherein said first light source includes one or more light emitting diodes (LED) and said second light source does not include light emitting diodes (LED).

11. The lighting system of claim 1, wherein said current splitter provides substantially zero current to said second light source when said one or more sensors detects a presence of one or more human or animal within said area.

12. The lighting system of claim 1, wherein said current splitter provides substantially zero current to said first light source when said one or more sensors does not detect a presence of one or more humans or animals within said area.

13. The lighting system of claim 1, wherein the UV light has a wavelength of about 222 nm.

14. The lighting system of claim 1, wherein the UV light has a wavelength of about 254 nm.

15. A method for controlling a lighting system, comprising:
   receiving a first signal from a first sensor, the first signal indicative of occupancy of a space;
   receiving a second signal from a second sensor, the second signal indicative of a presence of one or more predetermined micro-organisms within the space; and
   controlling a first light emitting diode (LED) array associated with visible light and a second LED array associated with UV light based at least in part on the first signal and the second signal.

16. The method of claim 15, wherein the UV light has a wavelength between about 220 nm and about 285 nm.

17. The method of claim 16, wherein the UV light has a wavelength of about 222 nm.

18. The method of claim 16, wherein the UV light has a wavelength of about 254 nm.

19. The method of claim 15, further comprising:
   dividing a total amount of current applied to said first and second LED arrays such that said first light emitting diode array receives a greater amount of current than said second light emitting diode array when said first signal indicates occupancy of said space.

* * * * *